(12) United States Patent
Tseng et al.

(10) Patent No.: US 7,927,301 B2
(45) Date of Patent: Apr. 19, 2011

(54) SAFETY SYRINGE

(76) Inventors: Hsi-Hsun Tseng, Chi-Lung (TW);
Chih-Ming Wang, Chi-Lung (TW);
Po-Liang Lee, Chi-Lung (TW);
Chun-Chieh Chuang, Chi-Lung (TW)

( * ) Notice: Subject to any disclaimer, the term of this patent is extended or adjusted under 35 U.S.C. 154(b) by 0 days.

(21) Appl. No.: 12/418,556

(22) Filed: Apr. 3, 2009

(65) Prior Publication Data
US 2010/0125252 A1 May 20, 2010

(30) Foreign Application Priority Data
Nov. 19, 2008 (TW) ................................ 97220724 U (51) Int. Cl.
*A61M 5/00* (2006.01)
(52) U.S. Cl. ........................................ 604/110; 604/195
(58) Field of Classification Search .................. 604/110, 604/218, 187
See application file for complete search history.

(56) References Cited

U.S. PATENT DOCUMENTS

| | | | |
|---|---|---|---|
| 2004/0199113 A1* | 10/2004 | Capes et al. | 604/110 |
| 2007/0066936 A1* | 3/2007 | Lam | 604/110 |
| 2007/0078402 A1* | 4/2007 | Yang | 604/187 |
| 2007/0135764 A1* | 6/2007 | Chen | 604/110 |
| 2007/0260181 A1* | 11/2007 | Smith et al. | 604/110 |

* cited by examiner

*Primary Examiner* — Kevin C Sirmons
*Assistant Examiner* — Brandy C Scott
(74) *Attorney, Agent, or Firm* — Stout, Uxa, Buyan & Mullins, LLP (57) ABSTRACT

A safety syringe includes an outer barrel, a needle unit, an outer barrel plug, an inner barrel, an inner barrel plug, a needle clamper, and a vacuum generating device. The needle unit is disposed within the front end of the outer barrel. The outer barrel plug is disposed within the outer barrel; the outer barrel plug is connected with the needle unit so as to fix the needle unit. The inner barrel plug is disposed within the front end of the inner barrel. The needle clamper is connected with the inner barrel plug. The needle clamper is able to clamp a rear opening of the needle unit. The vacuum generating device is disposed within the inner barrel, and the needle unit can be retracted into the inner barrel by the low pressure which is generated by the vacuum generating device.

11 Claims, 7 Drawing Sheets

SAFETY SYRINGE

BACKGROUND OF THE INVENTION

1. Field of the Invention

The present invention generally relates to a safety syringe, and more particularly to a safety syringe which has a vacuum generating device.

2. Description of the Prior Art

Figure 1:
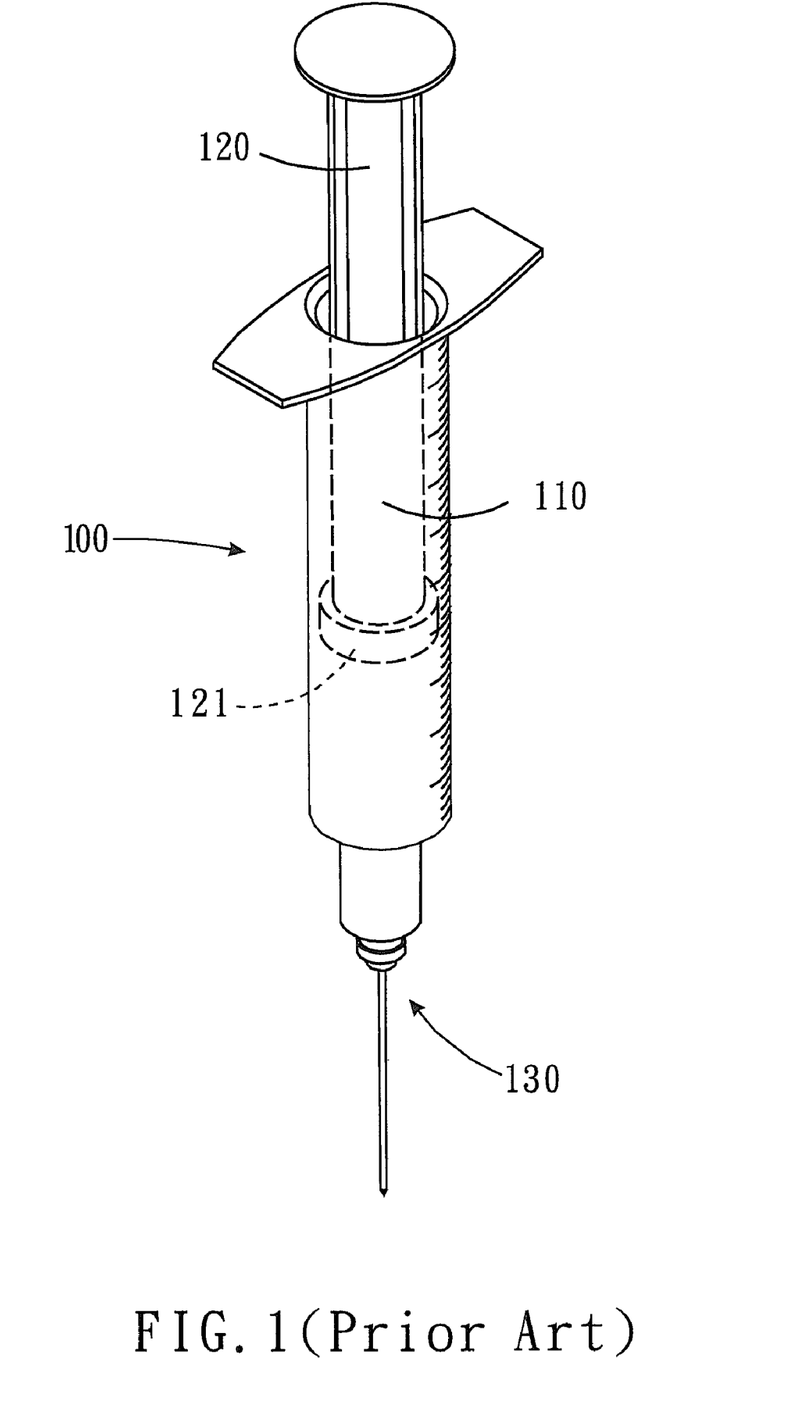
FIG. 1 shows a perspective view of a conventional syringe.

FIG. 1 shows a perspective view of a conventional syringe. The conventional syringe 100 includes an outer syringe barrel 110, a rod 120, and a needle unit 130. The needle unit 130 is fixed on the front end of the outer syringe barrel 110 by screw thread. The rod 120 has a plug portion 121. The plug portion 121 is in air-tight contact with the inner wall of the outer syringe barrel 110. When performing an injection process, the rod 110 is pushed toward the front end of the outer syringe barrel 110 by a user, and the medical solution within the syringe 100 can flow through an opening of the needle unit 130. After the injection process, the needle unit 130 should be enclosed with a needle sheath by the user manually. However, it is possible that the user may be stuck by the needle unit 130, and infection risk of the user is increased. Therefore, safety syringes with needles that can be retrieved automatically have been provided to prevent the user from risk of infection.

Generally, the needles of the safety syringes are retrieved automatically by low pressure. The low pressure is sealed within the safety syringe during the making process of the safety syringe. Before the safety syringe is used, the air is sucked gradually into the safety syringe, and the low pressure sealed within the safety syringe is also decreased gradually. Finally, the needles of the safety syringes may fail to be retrieved automatically because the low pressure is insufficient.

For the reason that there are disadvantages of the prior art as mentioned above, a need has existed to propose a novel safety syringe. The safety syringe has a vacuum generating device that is able to generate enough low pressure to prevent the situation where the needle of the safety syringe may fail to be retrieved automatically because of the low pressure not being adequate.

SUMMARY OF THE INVENTION

Accordingly, the present invention has been made in order to meet such a need as described above, and it is thus an object of the present invention to provide a safety syringe which has a suitable vacuum generating device. The vacuum generating device is able to generate enough low pressure to prevent the situation where a needle of the safety syringes may fail to be retrieved automatically because of insufficient pressure.

In order to achieve the above objects, the present invention provides a safety syringe that includes an outer barrel, a needle unit, an outer barrel plug, an inner barrel, an inner barrel plug, a needle clamper, and a vacuum generating device. The outer barrel has a front end and a rear end. The needle unit is disposed within the front end of the outer barrel. The outer barrel plug is disposed within the outer barrel; the outer barrel plug is connected with the needle unit so as to fix the needle unit. The inner barrel has a front end and a rear end. The inner barrel is inserted in the outer barrel through the rear end of the outer barrel. The inner barrel plug is disposed within the front end of the inner barrel. The needle clamper is connected with the inner barrel plug. The needle clamper is able to clamp a rear opening of the needle unit. The vacuum generating device is disposed within the inner barrel wherein the needle unit can be retracted into the inner barrel by low pressure generated by the vacuum generating device.

DETAILED DESCRIPTION OF THE INVENTION

The detailed description of the present invention will be discussed in the following embodiments, which are not intended to limit the scope of the present invention, but can be adapted for other applications. While drawings are illustrated in detail, it is appreciated that the quantity of the disclosed components may be greater or less than that disclosed, except where expressly restricting the amount of the components.

Figure 2A:
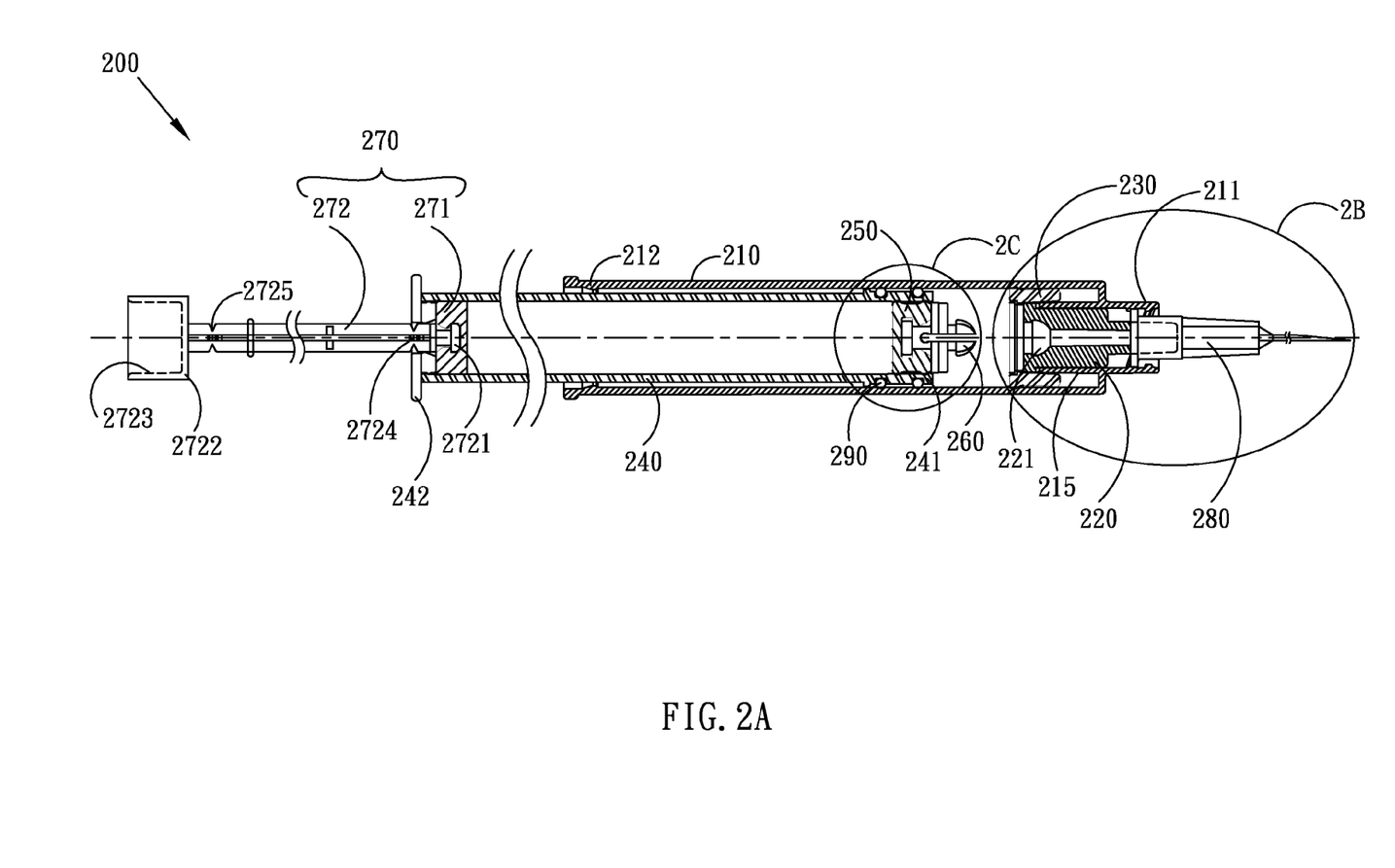
FIG. 2A shows a sectional view of a safety syringe in accordance with a preferred embodiment of the present invention.

FIG. 2A shows a sectional view of a safety syringe 200 in accordance with a preferred embodiment of the present invention. The safety syringe 200 includes an outer barrel 210, a needle unit 220, an outer barrel plug 230, an inner barrel 240, an inner barrel plug 250, a needle clamper 260, and a vacuum generating device 270. The outer barrel 210 has a front end 211 and a rear end 212. The inner barrel 240 has a front end 241 and a rear end 242. The inner barrel 240 is inserted in the outer barrel 210 through the rear end 212 of the outer barrel 210. The vacuum generating device 270 is disposed within the inner barrel 240.

Figure 2B:
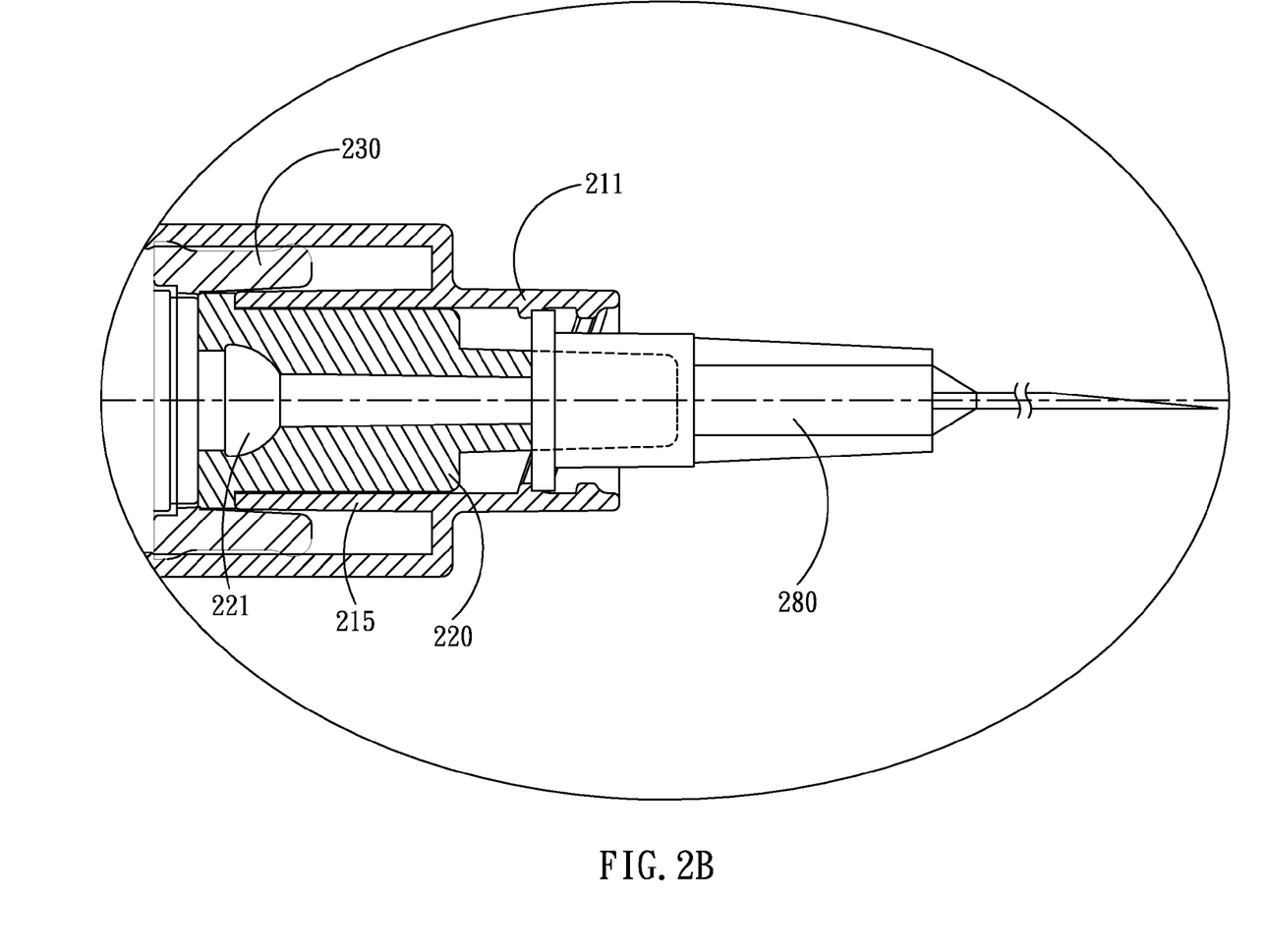
FIG. 2B shows an enlarged sectional view of the front end of the safety syringe shown in FIG. 2A.

FIG. 2B shows an enlarged sectional view of the front end of the safety syringe 200 shown in FIG. 2A. The needle unit 220 is disposed within the front end 211 of the outer barrel 210. The front end of the needle unit 220 is connected to a needle 280. The needle unit 220 has a rear opening 221. The outer barrel plug 230 is disposed within the outer barrel 210, wherein the outer barrel plug 230 is connected with the needle unit 220 so as to fix the needle unit 220. According to this embodiment, the outer barrel 210 has a connecting portion 215, and the needle unit 220 is disposed on the connecting portion 215. The connecting portion 215 is able to prevent the situation where the needle unit 220 is clamped by the outer barrel plug 230 so tightly that the needle unit 220 cannot be retracted into the inner barrel 240.

Figure 2C:
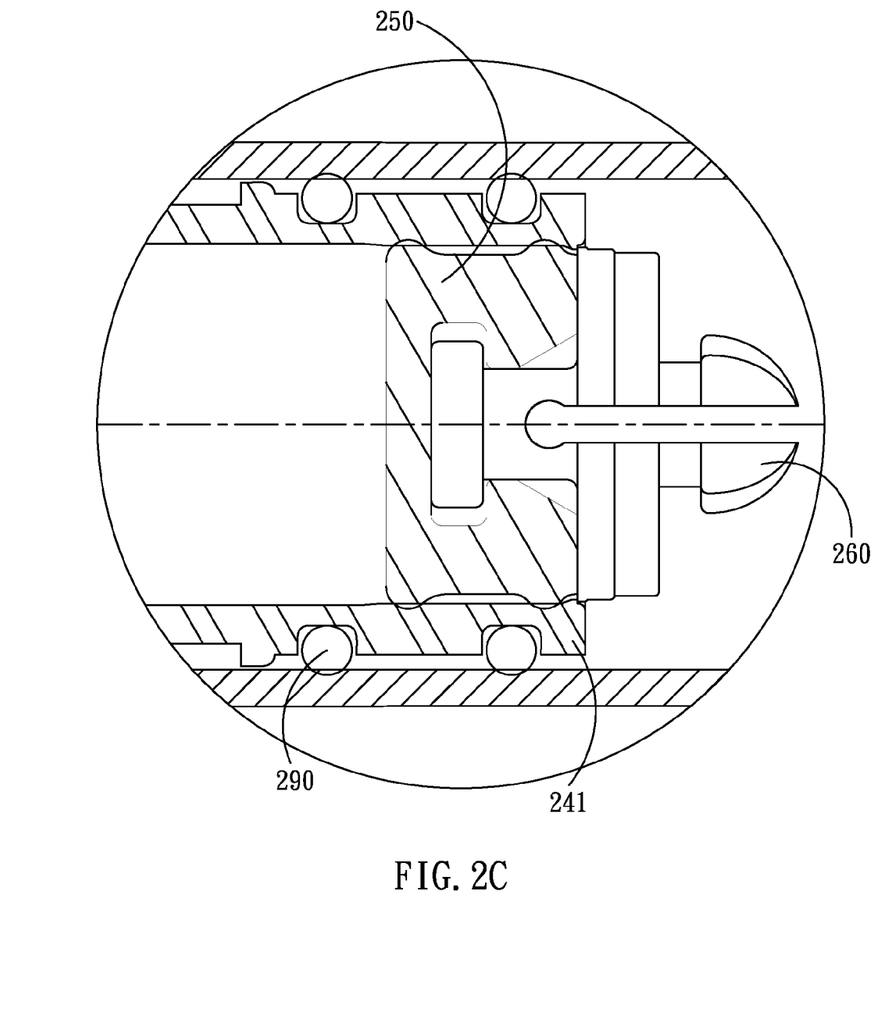
FIG. 2C shows an enlarged sectional view of the inner barrel shown in FIG. 2A.

FIG. 2C shows an enlarged sectional view of the inner barrel 240 shown in FIG. 2A. According to this embodiment, the safety syringe 200 includes at least one sealing ring 290. The sealing ring 290 is sleeved on the inner barrel 240 so as to provide an air-tight seal between the inner barrel 240 and the outer barrel 210. The sealing ring 290 can be an O-ring, but is not limited to this; the sealing ring 290 can be another structure that can provide an air-tight seal.

The inner barrel plug 250 is disposed within the front end 241 of the inner barrel 240. The needle clamper 260 is connected with the inner barrel plug 250. The needle clamper 260 is able to clamp the rear opening 221 of the needle unit 220. Referring to FIG. 2A, the vacuum generating device 270 is disposed within the inner barrel 240, wherein the needle unit 220 can be retracted into the inner barrel 240 by a low pressure which is generated by the vacuum generating device 270.

According to this embodiment, the vacuum generating device 270 has a vacuum plug 271 and a connecting rod 272. The vacuum plug 271 is made of a flexible material, which can be rubber, silica gel, or other flexible material. The connecting rod 272 is made of polypropylene. The connecting rod 272 has a front end 2721 and a rear end 2722. The front end 2721 of the connecting rod 272 is connected to the vacuum plug 271. The rear end 2722 of the connecting rod 272 has a seal portion 2723; the seal portion 2723 is capable of sealing the front end 211 of the outer barrel 210. The connecting rod 272 includes a first breakable portion 2724 and a second breakable portion 2725. The first breakable portion 2724 is near the front end 2721 of the connecting rod 272, and the second breakable portion 2725 is near the rear end 2722 of the connecting rod 272.

The vacuum plug 271 is in air-tight contact with the inner barrel 240. The connecting rod 272 is connected to the vacuum plug 271; the vacuum plug 271 is capable of moving by the connecting rod 272. When the vacuum plug 271 moves toward the rear end of inner barrel 240, low pressure is generated within the inner barrel 240. The magnitude of the low pressure is related to the diameter and the moving distance of the vacuum plug 271. For example, if the moving distance of the vacuum plug 271 is constant, when the diameter of the vacuum plug 271 is bigger, the magnitude of the low pressure is bigger. If the diameter of the vacuum plug 271 is constant, when the moving distance of the vacuum plug 271 is bigger, the magnitude of the low pressure is bigger. The diameter and the moving distance of the vacuum plug 271 are designed and adjusted by the real condition.

In this embodiment, the vacuum generating device 270 has a vacuum plug 271 and a connecting rod 272, but is not limited to this; the vacuum generating device 270 can be another device which is capable of generating low pressure.

Figure 2D:
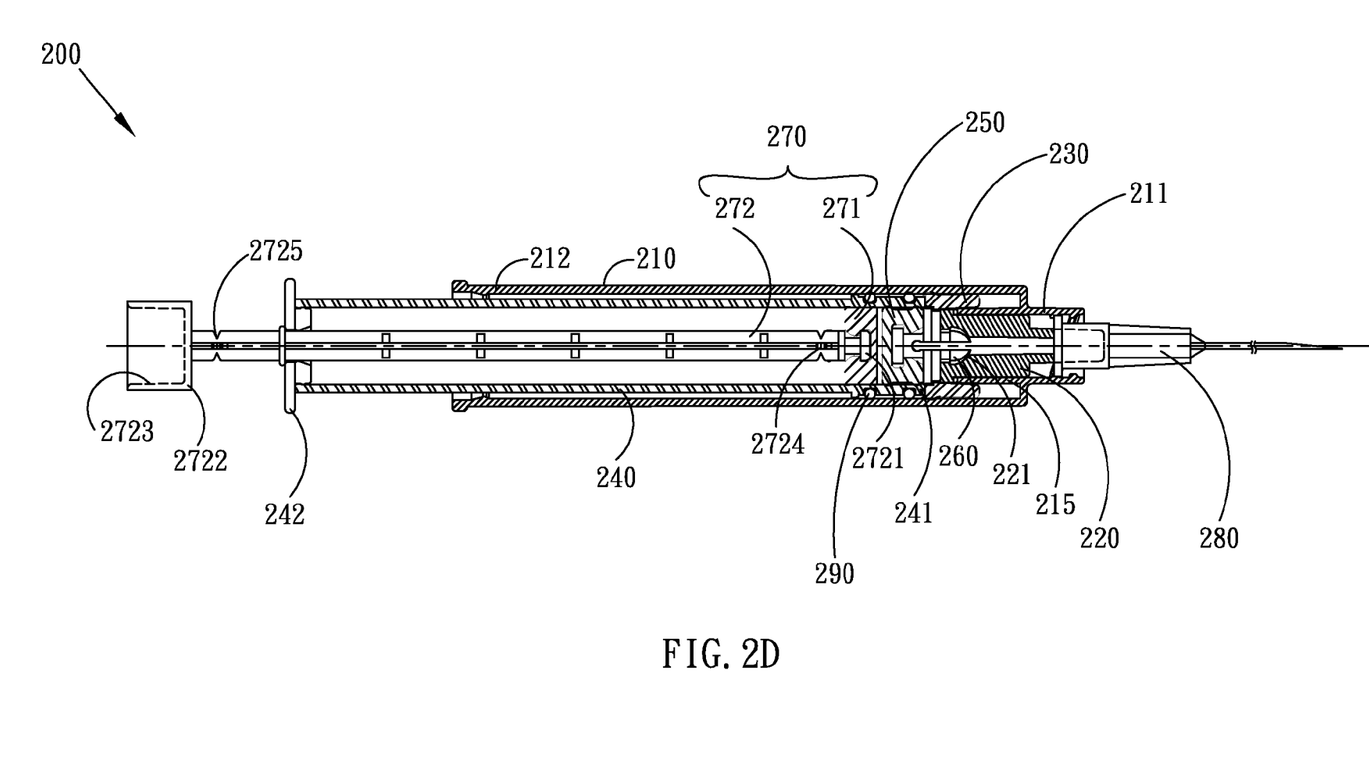
FIGS. 2D-2H show a use method of the safety syringe shown in FIG. 2A.
Figure 2E:
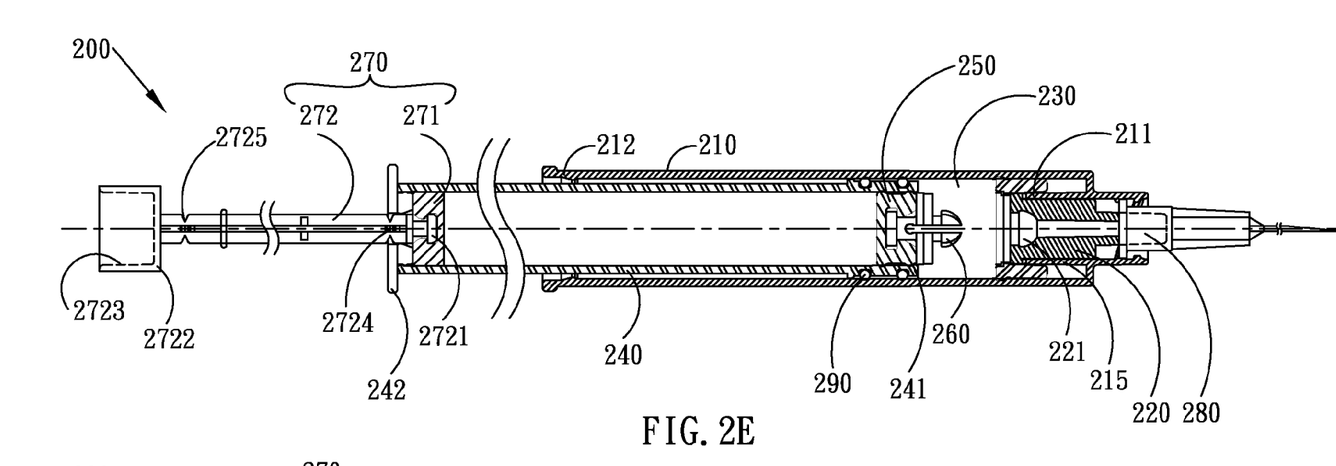
Figure 2F:
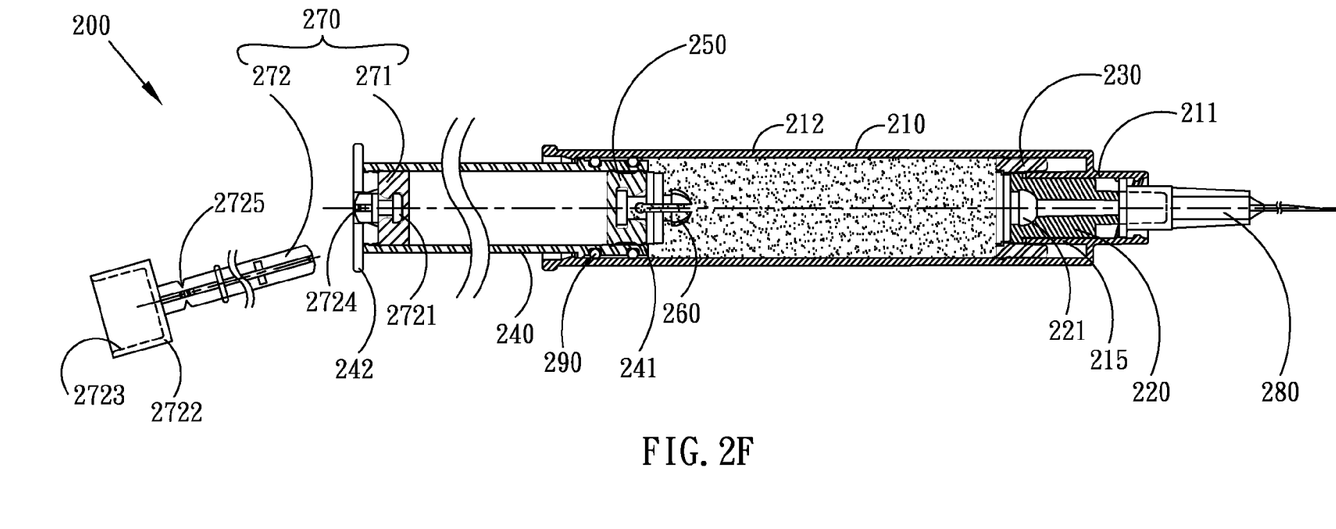

FIGS. 2D-2H show a use method of the safety syringe 200 shown in FIG. 2A. Referring to FIG. 2D and FIG. 2E, a user is capable of pulling the connecting rod 272, thus moving the vacuum plug 271 toward the rear end 242 of inner barrel 240. At the same time, suitable low pressure is generated within the inner barrel 240. Referring to FIG. 2F, the user is able to break the first breakable portion 2724 and remove the connecting rod 272. Then, medical solution can be refilled within the safety syringe 200.

Figure 2G:
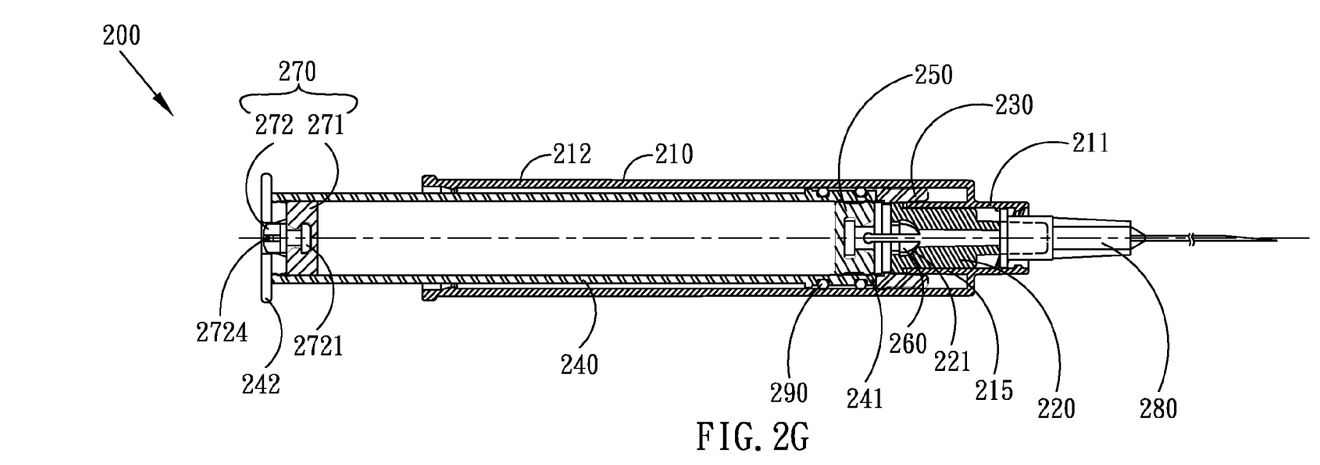

Referring to FIG. 2G, the user is able to perform the injection process; the inner barrel 240 moves toward the front end 211 of the outer barrel 210. When finishing the injection process, the needle clamper 260 is able to clamp the rear opening 221 of the needle unit 220, and the needle clamper 260 is able to seal the rear opening 221 of the needle unit 220. The inner barrel 240 continues moving toward the front end 211 of the outer barrel 210, and the inner barrel 240 is able to push the outer barrel plug 230 and release the connection between the outer barrel plug 230 and the needle unit 220. At the same time, the outer barrel plug 230 is sleeved on the connecting portion 215 of the outer barrel 210, and the needle unit 220 is clamped by the needle clamper 260.

The inner barrel 240 continues moving toward the front end 211 of the outer barrel 210. Because the inner barrel plug 250 is pushed by the connecting portion 215, the inner barrel plug 250 moves toward the inside of the inner barrel 240, and then the inner barrel plug 250 is retracted into the inner barrel 240 automatically by the low pressure within the inner barrel 240. Because the needle unit 220 is clamped by the needle clamper 260, the needle unit 220 is also retracted into the inner barrel 240 automatically.

Figure 2H:
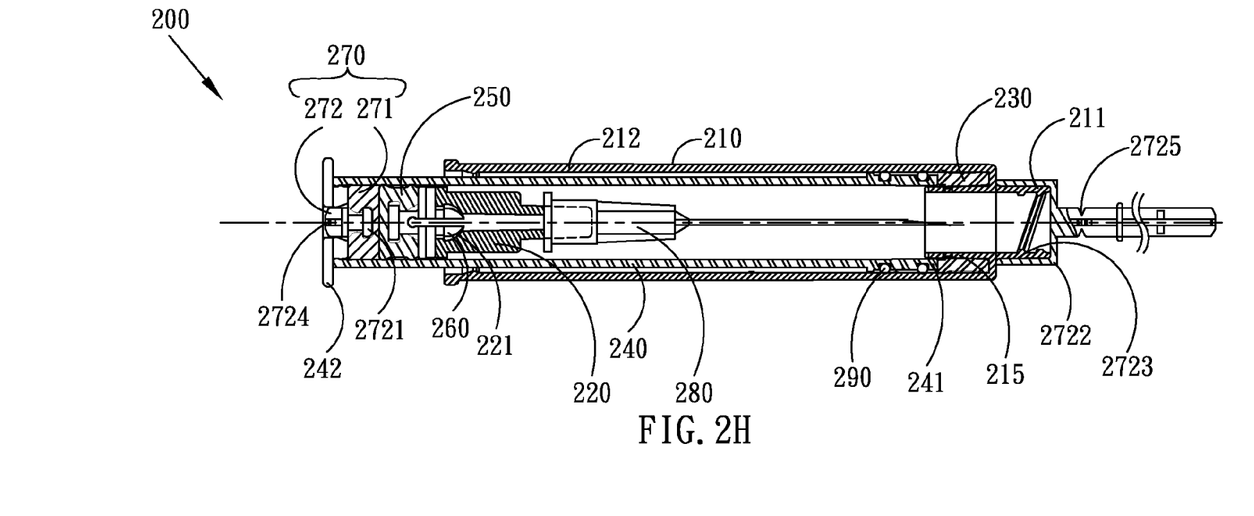

Referring to FIG. 2H, the user is able to put the seal portion 2723 on the front end 211 of the outer barrel 210 for sealing the front end 211 of the outer barrel 210. Therefore, the leakage of the medical solution within the safety syringe 200 can be avoided. Finally, the user is able to break the second breakable portion 2725 and remove the connecting rod 272. According to this embodiment, the design concept of the safety syringe 200 is suitable for a small volume syringe; for example, the volume of the safety syringe 200 can be 3 CC, 5 CC, or 10 CC. The volume of the safety syringe 200 is not limited; the design concept of the safety syringe 200 is also suitable for syringes of other volumes.

By using the safety syringe of the present invention, the vacuum generating device is able to generate enough low pressure for retrieving the needle automatically. The risk of infection to the user and the situation where the needle of the safety syringes may fail to be retrieved automatically can both be avoided.

Although specific embodiments have been illustrated and described, it will be appreciated by those skilled in the art that various modifications may be made without departing from the scope of the present invention, which is intended to be limited solely by the appended claims.

What is claimed is:

1. A safety syringe comprising: an outer barrel, said outer barrel having a front end and a rear end; a needle unit, said needle unit being disposed within said front end of the outer barrel; an outer barrel plug, said outer barrel plug being disposed within said outer barrel, wherein said outer barrel plug is connected with said needle unit so as to fix said needle unit; an inner barrel, said inner barrel having a front end and a rear end, wherein said inner barrel is inserted in said outer barrel through said rear end of said outer barrel; an inner barrel plug, said inner barrel plug being disposed within said front end of said inner barrel; a needle clamper, said needle clamper being connected with said inner barrel plug, wherein said needle clamper is able to clamp a rear opening of said needle unit; and a vacuum generating device, wherein said vacuum generating device comprises a vacuum plug, said vacuum plug is disposed within said inner barrel, both said vacuum plug and said inner barrel plug are capable of adjusting the volume defined by said vacuum plug, said inner barrel, and said inner barrel plug for generating low air pressure before injection process, the volume is adjusted by the distance between said vacuum plug and said inner barrel plug, and said needle unit can be retracted into said inner barrel by said low air pressure, said low air pressure maintains constant air pressure until said needle unit is retracted into said inner barrel, said vacuum plug is in air-tight contact with said inner barrel whereby when said vacuum plug moves toward said rear end of said inner barrel said low pressure is generated within said inner barrel, said vacuum generating device comprises a connecting rod, said connecting rod is connected to said vacuum plug, said vacuum plug is capable of moving by said connecting rod, said connecting rod comprises a front end and a rear end, said front end of said connecting rod is connected to said vacuum plug, and said connecting rod comprises a breakable portion.

2. The safety syringe according to claim 1, wherein said breakable portion comprises a first breakable portion, and said first breakable portion is near said front end of said connecting rod.

3. The safety syringe according to claim 1, wherein said connecting rod comprises a second breakable portion, said second breakable portion is near said rear end of said connecting rod, said rear end of said connecting rod has a seal portion, and said seal portion is capable of sealing said front end of said outer barrel.

4. The safety syringe according to claim 1, wherein said connecting rod is made of polypropylene.

5. The safety syringe according to claim 1, wherein said vacuum plug is made of a flexible material.

6. The safety syringe according to claim 5, wherein said flexible material is rubber.

7. The safety syringe according to claim 5, wherein said flexible material is silica gel.

8. The safety syringe according to claim 1, wherein said outer barrel comprises a connecting portion, and said needle unit is disposed on said connecting portion.

9. The safety syringe according to claim 1, further comprising a needle, a front end of said needle unit being connected to said needle.

10. The safety syringe according to claim 1, further comprising a sealing ring, wherein said sealing ring is sleeved on said inner barrel so as to provide air-tight seal between said inner barrel and said outer barrel.

11. The safety syringe according to claim 1, wherein said sealing ring is an O-ring.

* * * * *